United States Patent
McCavit et al.

(10) Patent No.: US 8,783,888 B2
(45) Date of Patent: Jul. 22, 2014

(54) FLAMELESS CANDLE WITH FRAGRANCE DIFFUSION

(75) Inventors: Kim Irwin McCavit, St. Joseph, MI (US); Robert Hutton Ray, Harvard, IL (US); Bernard Fournier, Delson (CA); Bradford Brian Jensen, St. Joseph, MI (US)

(73) Assignee: Winvic Sales Inc., Markham, Ontario (CA)

( * ) Notice: Subject to any disclaimer, the term of this patent is extended or adjusted under 35 U.S.C. 154(b) by 109 days.

(21) Appl. No.: 13/185,149

(22) Filed: Jul. 18, 2011

(65) Prior Publication Data

US 2012/0020052 A1    Jan. 26, 2012

Related U.S. Application Data

(60) Provisional application No. 61/365,649, filed on Jul. 20, 2010.

(51) Int. Cl.
| | |
|---|---|
| *F21V 33/00* | (2006.01) |
| *F21S 6/00* | (2006.01) |
| *A61L 9/12* | (2006.01) |
| *F21S 9/02* | (2006.01) |
| *F21S 10/04* | (2006.01) |
| *F21W 121/00* | (2006.01) |
| *F21Y 101/02* | (2006.01) |

(52) U.S. Cl.
CPC ............. *F21V 33/0028* (2013.01); *F21S 6/001* (2013.01); *A61L 9/122* (2013.01); *F21W 2121/00* (2013.01); *F21S 9/02* (2013.01); *F21S 10/04* (2013.01); *F21Y 2101/02* (2013.01)
USPC .............................. 362/96; 362/162; 362/392

(58) Field of Classification Search
USPC ............................ 362/96, 161, 364, 392, 810
See application file for complete search history.

(56) References Cited

U.S. PATENT DOCUMENTS

| | | | |
|---|---|---|---|
| 5,126,078 | A | 6/1992 | Steiner et al. |
| 5,167,877 | A | 12/1992 | Pai |

(Continued)

FOREIGN PATENT DOCUMENTS

| | | |
|---|---|---|
| CA | 2 530 606 A1 | 1/2005 |
| CA | 2 555 031 A1 | 8/2005 |

OTHER PUBLICATIONS

Patent Cooperation Treaty, Notification of Transmittal of the International Search Report and the Written Opinion of the International Searching Authority, or the Declaration, in International application No. PCT/US2011/044492, dated Mar. 15, 2012. (23 pages).

(Continued)

*Primary Examiner* — John A Ward
(74) *Attorney, Agent, or Firm* — McAndrews, Held & Malloy, Ltd.

(57) ABSTRACT

According to embodiments of the present invention, a flameless candle includes a housing, a reservoir, and a lamp. The reservoir can retain a fragrant source (e.g., solid, liquid, or mix thereof. The housing has a hollow region and a recessed area within the top surface of the housing. The recessed area is bounded by a bottom surface and a sidewall. There one or more vent holes in the sidewall. If there is a plurality of vent holes, then they may encircle the sidewall. The vent hole(s) allow an airflow from the hollow region and into the recessed area above the fragrant source. The lamp can emit a light through the bottom surface of the recessed area and through fragrant source.

23 Claims, 6 Drawing Sheets

(56) References Cited

U.S. PATENT DOCUMENTS

| | | |
|---|---|---|
| 5,201,025 A | 4/1993 | Landesberg |
| 5,376,338 A | 12/1994 | Zlotnik |
| 5,402,517 A | 3/1995 | Gillett et al. |
| D359,346 S | 6/1995 | Martin |
| 5,547,616 A | 8/1996 | Dancs et al. |
| 5,647,052 A | 7/1997 | Patel et al. |
| 5,651,942 A | 7/1997 | Christensen |
| 5,662,835 A | 9/1997 | Collingwood |
| 5,805,768 A | 9/1998 | Schwartz et al. |
| 5,903,710 A | 5/1999 | Wefler et al. |
| 5,970,643 A | 10/1999 | Gawel, Jr. |
| 5,976,503 A | 11/1999 | Martin et al. |
| 6,044,202 A | 3/2000 | Junkel |
| 6,106,786 A | 8/2000 | Akahoshi |
| 6,123,935 A | 9/2000 | Wefler et al. |
| 6,141,496 A | 10/2000 | Sundberg et al. |
| 6,197,263 B1 | 3/2001 | Blount |
| 6,302,559 B1 | 10/2001 | Warren |
| 6,361,752 B1 | 3/2002 | Demarest et al. |
| 6,371,450 B1 | 4/2002 | Davis et al. |
| 6,446,583 B2 | 9/2002 | Vieira |
| 6,450,419 B1 | 9/2002 | Martens, III et al. |
| 6,478,440 B1 | 11/2002 | Jaworski et al. |
| 6,487,367 B2 | 11/2002 | Vieira |
| 6,555,068 B2 | 4/2003 | Smith |
| 6,569,387 B1 | 5/2003 | Furner et al. |
| 6,592,104 B2 | 7/2003 | Cox |
| 6,603,924 B2 | 8/2003 | Brown et al. |
| 6,631,888 B1 | 10/2003 | Prueter |
| 6,661,967 B2 | 12/2003 | Levine et al. |
| 6,713,024 B1 | 3/2004 | Arnell et al. |
| 6,719,217 B1 | 4/2004 | Tawara et al. |
| 6,728,478 B2 | 4/2004 | Cox et al. |
| 6,854,717 B2 | 2/2005 | Millan |
| 6,912,355 B2 | 6/2005 | Vieira |
| 6,913,733 B2 | 7/2005 | Hardy et al. |
| 6,966,665 B2 | 11/2005 | Limburg et al. |
| 7,014,818 B2 | 3/2006 | Rymer |
| 7,093,949 B2 | 8/2006 | Hart et al. |
| 7,204,870 B2 | 4/2007 | Zobele et al. |
| D551,750 S | 9/2007 | Wefler |
| 7,281,811 B2 | 10/2007 | Thuot Rann et al. |
| 7,309,387 B2 | 12/2007 | He et al. |
| 7,318,653 B2 | 1/2008 | Chien |
| 7,341,698 B2 | 3/2008 | Pedrotti et al. |
| 7,377,493 B2 | 5/2008 | Thomas |
| 7,481,571 B2 | 1/2009 | Bistritzky et al. |
| 7,503,668 B2 * | 3/2009 | Porchia et al. ............... 362/161 |
| 7,520,635 B2 | 4/2009 | Wolf et al. |
| 7,544,331 B1 | 6/2009 | Pettaway |
| 7,652,436 B2 | 1/2010 | Dowling et al. |
| 7,670,035 B2 | 3/2010 | Tsai |
| 7,687,744 B2 | 3/2010 | Walter et al. |
| 7,723,899 B2 | 5/2010 | Blandino et al. |
| 7,744,833 B2 | 6/2010 | Varanasi et al. |
| 7,824,627 B2 * | 11/2010 | Michaels et al. ............. 422/128 |
| 2004/0052076 A1 | 3/2004 | Mueller et al. |
| 2004/0264169 A1 | 12/2004 | Limburg |
| 2005/0169666 A1 * | 8/2005 | Porchia et al. ............... 399/111 |
| 2005/0169812 A1 * | 8/2005 | Helf et al. .................... 422/123 |
| 2005/0285538 A1 * | 12/2005 | Jaworski et al. ............... 315/76 |
| 2006/0120080 A1 * | 6/2006 | Sipinski et al. ............... 362/253 |
| 2006/0193611 A1 | 8/2006 | Ruiz Ballesteros et al. |
| 2007/0127249 A1 | 6/2007 | Medley |
| 2007/0177394 A1 | 8/2007 | Vock et al. |
| 2007/0183940 A1 | 8/2007 | Yamamoto et al. |
| 2008/0031784 A1 | 2/2008 | Bistritzky |
| 2008/0036332 A1 * | 2/2008 | Helf et al. .................... 310/311 |
| 2008/0130266 A1 | 6/2008 | DeWitt et al. |
| 2009/0122516 A1 | 5/2009 | Yang |

OTHER PUBLICATIONS

Photographs and accompanying inventor declaration dated Sep. 7, 2011.

\* cited by examiner

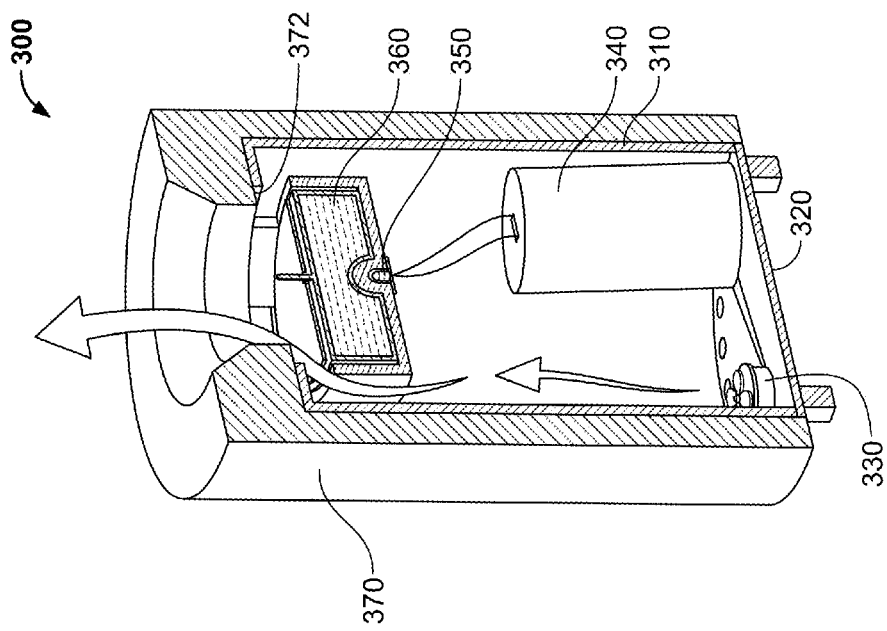
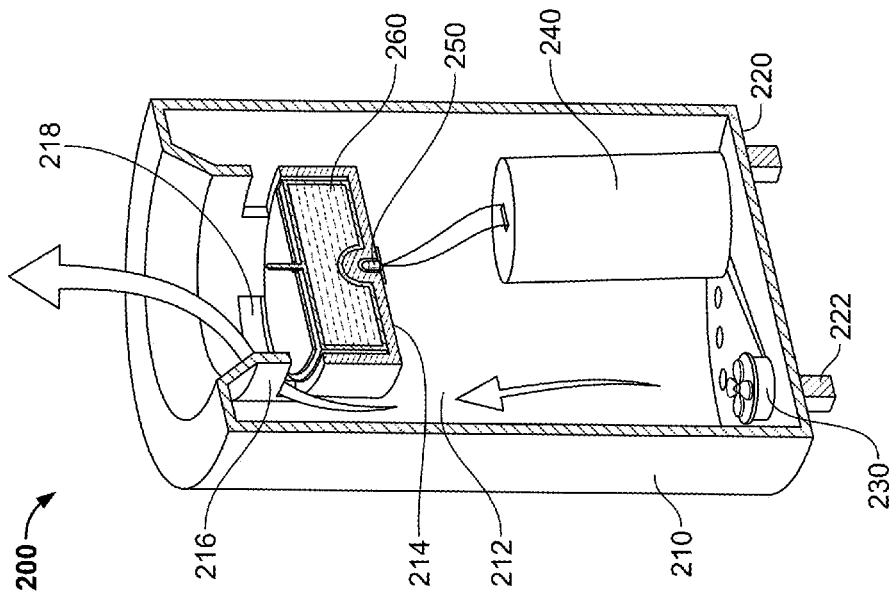

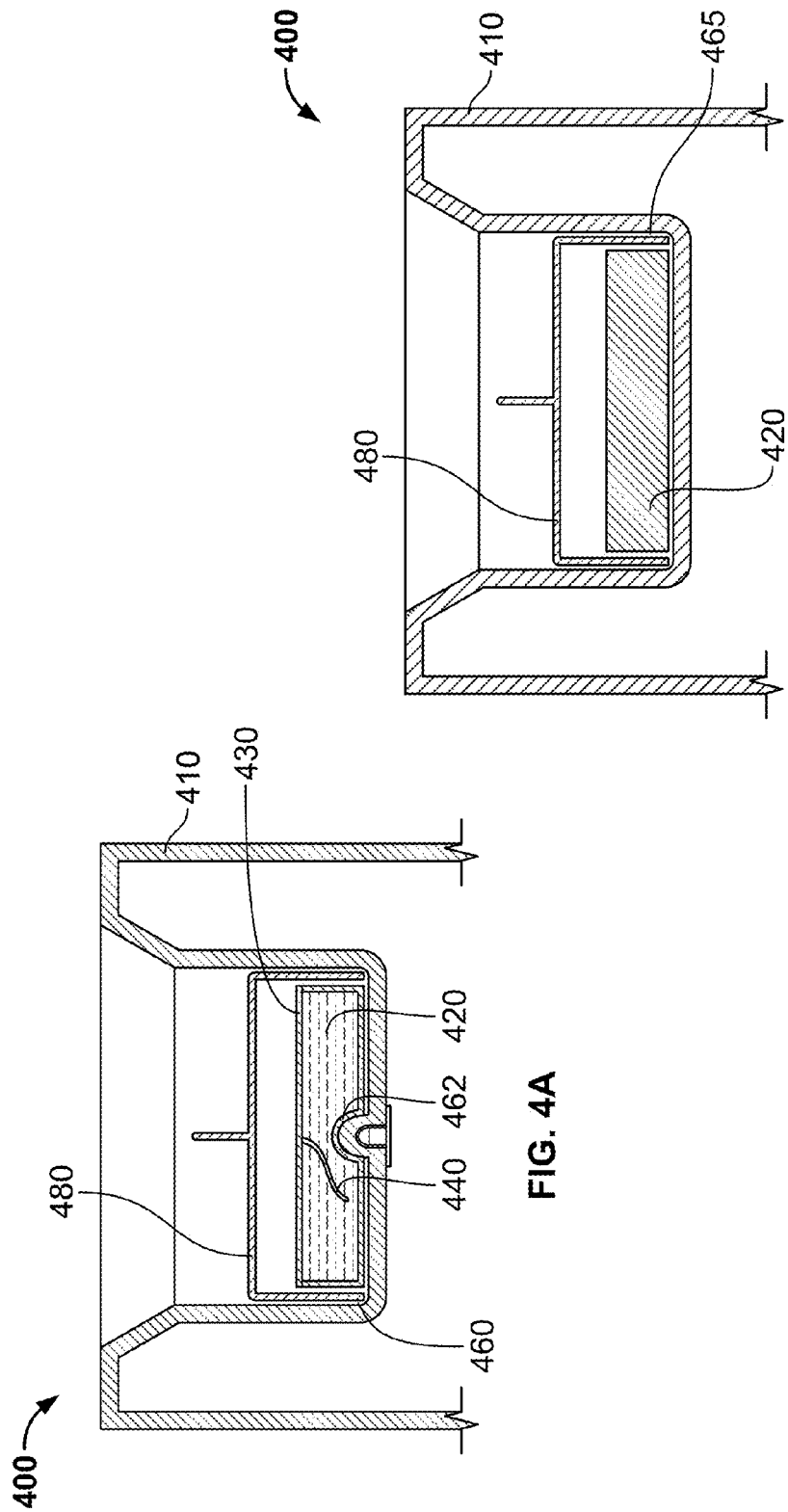

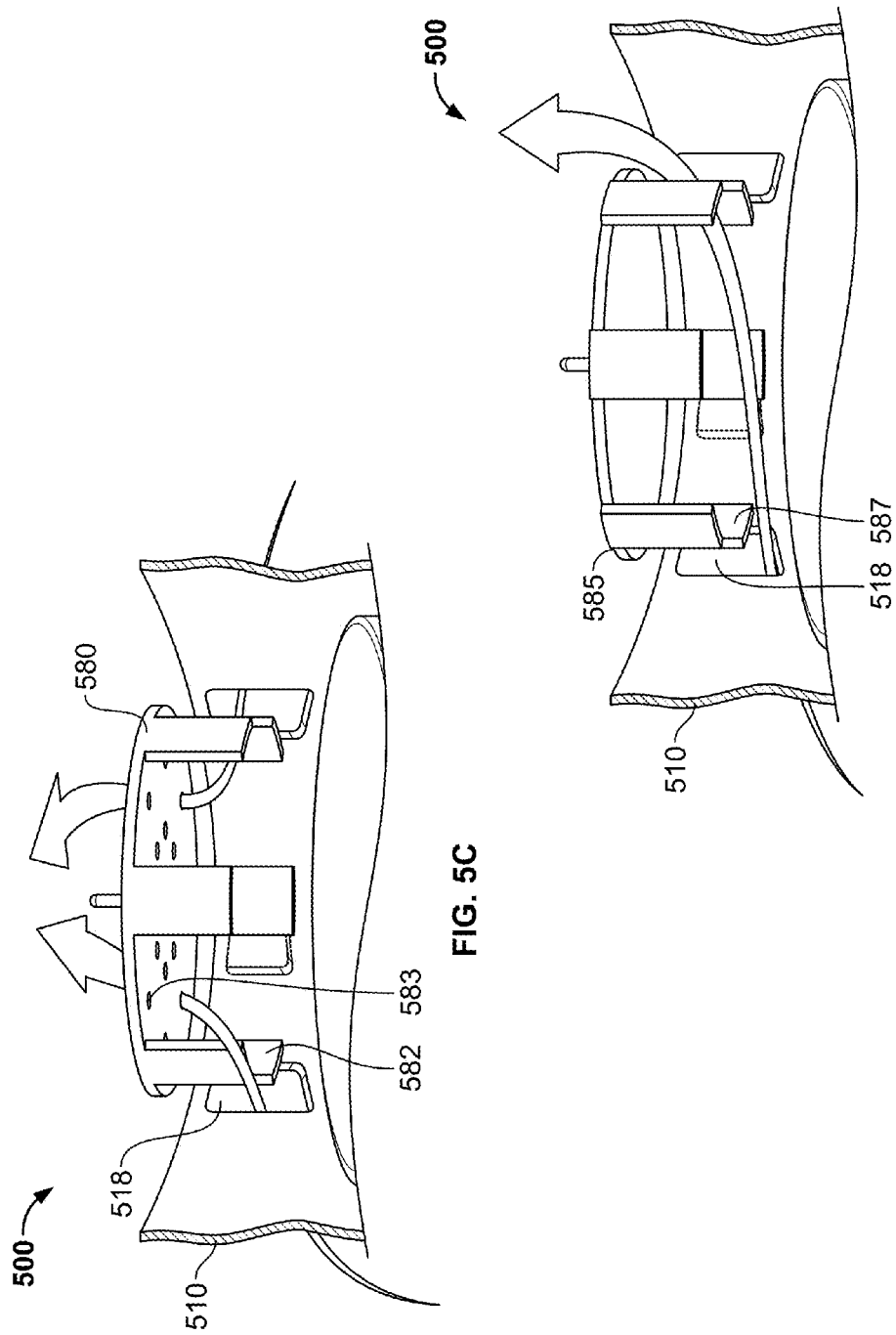

FLAMELESS CANDLE WITH FRAGRANCE DIFFUSION

RELATED APPLICATIONS

This application claims priority to U.S. Provisional Patent Application No. 61/365,649 filed on Jul. 19, 2010, which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Generally, the present application relates to flameless candles. Particularly, the present application relates to techniques for diffusing fragrance into the living space atmosphere from a flameless candle.

Flameless candles may emulate conventional candles in their appearance and behavior without having the risk associated with a flame. Certain flameless candles also attempt to emulate conventional fragrance-emitting candles. One technique used by such flameless candles is to use a heater element to diffuse a fragrant substance. However, such heating can accelerate thermal decay of fragrant materials or change their character. Additionally, such heater elements may consume a relatively large amount of power, especially if the candle is portable.

Other flameless candles may employ air freshener wicks which may cause fractional distillation evaporation from the moistened wick surface. Such an effect may change the character of the fragrance over time.

Some flameless candles may have a fan. However, it may be difficult or expensive to vary the amount of airflow generated by the fan. For example, additional circuitry may be required to vary the speed of the fan. Furthermore, the fan may blow air directly into or onto a fragrant material. This may result in a fragrance that is relatively intense and may cause the fragrant material to lose its fragrance more quickly.

Thus, it may be desirable to have a flameless candle that solves these and other problems.

BRIEF SUMMARY OF THE INVENTION

According to embodiments of the present invention, a flameless candle includes a housing, a reservoir, and a lamp. The reservoir can retain a fragrant source including a fragrant substance (e.g., solid, liquid, or mix thereof) and may be integrated with the housing. The housing has a hollow region and a recessed area within the top surface of the housing. The recessed area is bounded by a bottom surface and a sidewall. There are one or more vent holes in the sidewall. If there is a plurality of vent holes, then they may encircle the sidewall. The vent hole(s) allow an airflow from the hollow region and into the recessed area above the fragrant source. The lamp can emit a light through the bottom surface of the recessed area and through the fragrant source. In an embodiment, the bottom surface of the reservoir has a raised portion that can accommodate the lamp underneath the reservoir.

In an embodiment, the flameless candle has an outer shell encompassing the housing. The outer shell may have an eave that can conceal the vent holes from being visible when the flameless candle is viewed from the top. The outer shell may include wax.

In an embodiment, the candle includes a cover that can cover the reservoir. When covering the reservoir, the top surface of the reservoir may define a bottom surface of a well in the flameless candle. The cover may have a handle. The handle may resemble a wick. In an embodiment, the cover has perforations that allow airflow from the reservoir and into the living space atmosphere. In another embodiment, the top surface of the cover has a radius less than a radius of the reservoir. A gap is formed and it allows the airflow from the reservoir and into the living space atmosphere. In an embodiment, the cover has legs that support the cover. The legs may also control the airflow through the vent hole(s) in response to the cover being rotated.

If the fragrant source is a liquid, the candle may include a pad that can provide the liquid to the airflow. The candle may also have a wick to draw the fragrant liquid from the reservoir and into the pad.

The flameless candle may also have a base that can engage with a bottom portion of the housing. The base may have feet that elevate the housing above a resting surface. The base may also have one or more holes that allow the airflow from the living space atmosphere and into the hollow region. A fan may be positioned proximate to the housing bottom (e.g., mounted on the base) and may promote the airflow.

According to embodiments of the present invention, a flameless candle includes a lamp, a fragrance generating system, and an electronics portion. The electronics portion can periodically illuminate the lamp. The electronics portion also periodically operates the fragrance generating system independently from the lamp. As an example, the electronics portion may periodically illuminate and operate the lamp and fragrance generating system according to a 24-hour timer.

According to embodiments of the present invention, a flameless candle includes a housing. The housing has a hollow region within the housing and a recessed area within a top surface of the housing. The recessed area has a sidewall. The recessed area is configured to retain a fragrant source including a fragrant substance and a headspace above the fragrant source. The air in the headspace is at least partially saturated with the fragrant substance. There is a vent hole in the sidewall of the recessed area. The vent hole is configured to allow an airflow from the hollow region and into the recessed area above the headspace. The airflow may draw the fragrant substance from the air in the headspace through the Venturi effect.

BRIEF DESCRIPTION OF SEVERAL VIEWS OF THE DRAWINGS

FIG. 2 shows a cross-sectional view of a portion of a flameless candle, according to an embodiment of the present invention.

FIG. 3 shows a cross-sectional view of a flameless candle, according to an embodiment of the present invention.

FIG. 4A shows a reservoir for holding a fragrant source, according to an embodiment of the present invention.

FIG. 4B shows a reservoir for holding a fragrant source, according to an embodiment of the present invention.

FIG. 5C shows a flameless candle including a cover for a reservoir for holding a fragrant source, according to an embodiment of the present invention.

FIG. 5D shows a flameless candle including a cover for a reservoir for holding a fragrant source, according to an embodiment of the present invention.

Figure 1:
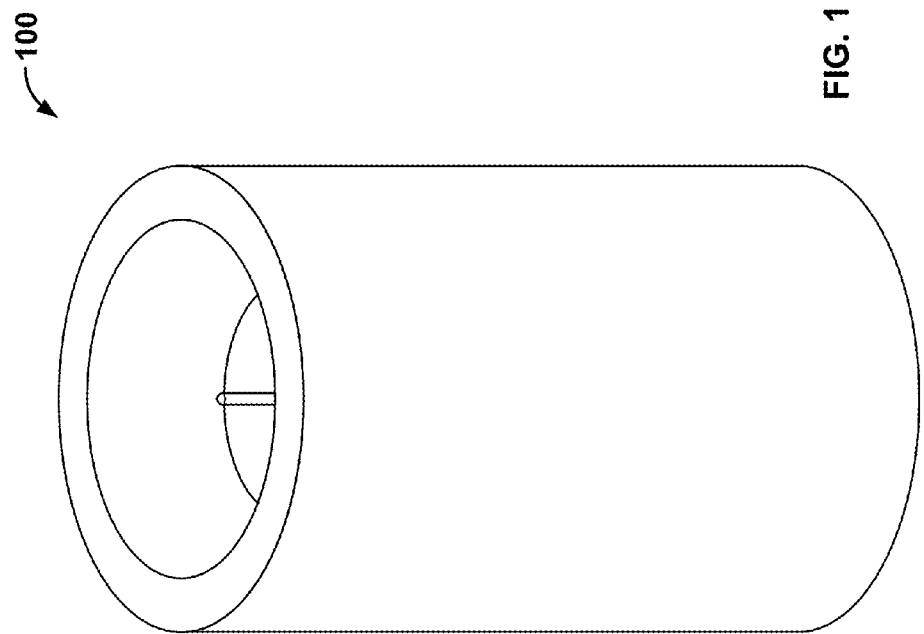
FIG. 1 shows a flameless candle, according to an embodiment of the present invention.

The foregoing summary, as well as the following detailed description of certain embodiments of the present invention, will be better understood when read in conjunction with the appended drawings. For the purposes of illustration, certain embodiments are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION OF THE INVENTION

FIG. 1 shows a perspective view of a flameless candle 100, according to an embodiment of the present invention. The flameless candle 100 may appear as a conventional candle. For example, the candle 100 may have a lamp that emits a flickering light. The flameless candle 100 may also emit a fragrance.

FIG. 2 shows a cross-sectional view of a flameless candle 200, according to an embodiment of the present invention. The flameless candle 200 may include a housing 210, a base 220, a fan 230, a battery/electronics compartment 240, a lamp 250, and a reservoir 260.

The housing 210 may have a hollow region 212 within the housing 210. The housing 210 may also have a recessed area within a top surface of the housing 210. A portion of the recessed area may form a well in the top of the housing 210. The well may provide the appearance of a candle that has been used. The recessed area may be bounded by a bottom surface 214 and a sidewall 216. A sidewall 216 may be vertical or at another angle. A sidewall 216 and/or a bottom surface 214 may have a variety of surface shapes, such as a concave surface or a flat surface. There may be one or more vent holes 218 in the sidewall 216. The vent hole(s) 218 may hydrodynamically couple the hollow region 212 and the recessed area. If there is a plurality of vent holes 218, they may encircle the sidewall 216.

The reservoir 260 may be located within the recessed area. The reservoir 260 may be able to retain a fragrant source. A lamp 250, (e.g., a light-emitting diode—LED or an incandescent bulb) may be located below the bottom surface 214 of the recessed area. The bottom surface 214 may have a raised portion to accommodate the lamp 250. The lamp 250 may emit a flickering light. The lamp 250 may be variable in its intensity or produce other effects, e.g., light of different colors. For example, the lamp 250 may vary in brightness in a pseudo-random or random manner to simulate the flickering of a flame. The lamp 250 may be able to emit light through the bottom surface 214 of the recessed area and through the fragrant source.

A battery and/or an electronics system may be provided to provide power to the lamp 250 and the fan 230. The battery or electronics system may be housed in a compartment 240. One or more switches may be provided (e.g., on the bottom surface of the base 220) to switch power to the lamp 250 and/or the fan 230. The electronics system may also be located in the fan 230 or in the lamp 250. The electronics may cause the lamp 250 to flicker to simulate a conventional flamed candle.

The electronics system may implement a timer to provide timed control to the lamp 250 or fan 230. For example, the electronics system may implement a twenty-four hour timer. The electronics system may periodically illuminate the lamp and/or operate the fragrance generating system. For example, the fragrance generating system could be operated together with the lamp. Alternatively, the fragrance generating system could be operated independently or separately from the lamp. Switches or actuators may allow a user to configure how timed control of the fragrance generating system and the lamp will operate. For example, a switch may instruct the electronics system to periodically illuminate the lamp over a 24-hour cycle—5 hours on and 19 hours off. A switch may instruct the electronics system to periodically drive the fan to operate the fragrance generating system over the same 24-hour cycle, but on a different periodic schedule.

A fan 230 may be located on the base 220. The base 220 may engage with a bottom portion of the housing 210. The base 220 may have holes so that air may be drawn into the hollow region 212 from the living space atmosphere. The fan 230 may promote airflow through the flameless candle. The fan 230 may have adjustable speeds. The base 220 may have feet 222 to elevate the flameless candle above a resting surface in order to facilitate the airflow from the living space atmosphere and into the hollow region 212.

The fan 230 may promote airflow through the holes in the base 220. The airflow may then pass through the hollow region 212 and then through the vent hole 218. The airflow may then pass into the recessed area and over the fragrant source before passing into the living space atmosphere.

FIG. 3 shows a cross-sectional view of a flameless candle 300, according to an embodiment of the present invention. Similar to flameless candle 200, the flameless candle 300 may include a housing 310, a base 320, a fan 330, a battery compartment 340, a lamp 350, and a reservoir 360.

The flameless candle 300 also may have an outer shell 370. The outer shell 370 may encompass the housing 310. The outer shell 370 may include wax, a waxen, or a simulated wax material to emulate a conventional candle. The outer shell 370 may have an eave 372. The eave 372 may conceal the vent holes 318 from being visible when the flameless candle 300 is viewed from the top. Note, a similar eave feature could be implemented in flameless candle 200.

The combination of the housing 310 and the outer shell 370 may form various aspects of a recessed area similar to the one shown in FIG. 2. For example, the bottom surface of the recessed area may be formed by the housing 310. As another example, the sidewall of the recessed area may be formed by both the housing 310 and the outer shell 370.

FIGS. 4A and 4B show a flameless candle 400 having different reservoirs 460 and 465 for holding a fragrant source 420, according to embodiments of the present invention. There may be a variety of options for a fragrant source 420, such as volatile fragrance enhanced mediums, including air freshener gels, solids, pads, and the like. Other examples include liquid dilutions of such mediums, including refresher oils and cartridges. The fragrant source 420 may be replaced or removed. The reservoirs 460, 465 may be similar to reservoirs 260 or 360.

FIG. 4A shows a reservoir 460 nested within a housing 410. The reservoir 460 is shown as a separate component from the housing 410. The fragrant source 420 is shown as a liquid. A pad 430 and a real wick 440 may facilitate diffusion of the fragrant liquid source 420. The real wick 440 may draw the fragrant liquid source 420 into the pad 430. As further illustrated in FIG. 4A, the reservoir 460 may have a raised portion 462. The raised portion 462 may mate with a corresponding raised portion in the housing 410. A cover 480 may cover the reservoir 460. Covers, such as cover 480 are discussed in more detail in conjunction with FIGS. 5A and 5B. The top surface of the cover 480 may define a bottom surface of a well in the flameless candle. The well may be in the upper region of the recessed area, while the reservoir 460 may occupy the lower region of the recessed area. The cover 480 may be inserted or removed to access the fragrant source 420.

FIG. 4B is provided to further illustrate various design parameters for a reservoir. For example, reservoir 465 is shown as being integrated or being a part of the housing 410. The fragrant source 420 is shown as a solid. FIG. 4B also shows a bottom surface without a raised portion. Various aspects of the reservoirs 460, 465 can be mixed, matched, modified, etc. Thus FIGS. 4A and 4B, taken individually and together, illustrate various embodiments of a reservoir.

Figure 5B:
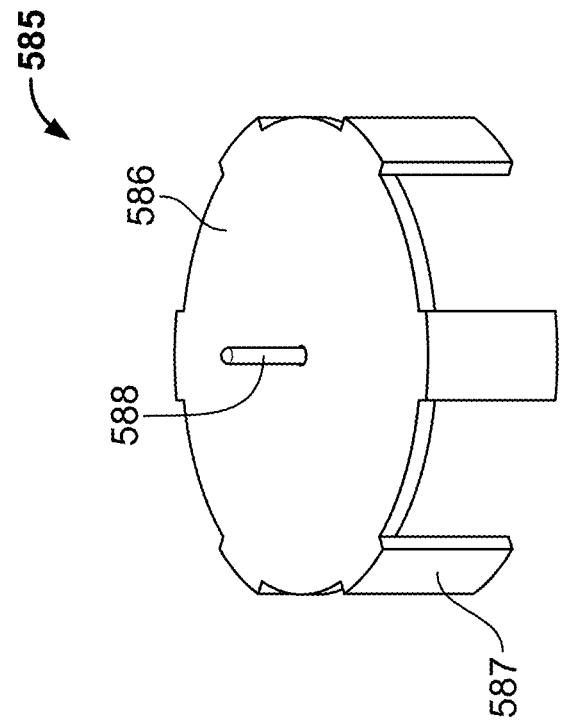
FIG. 5B shows a cover for a reservoir for holding a fragrant source, according to an embodiment of the present invention.
Figure 5A:
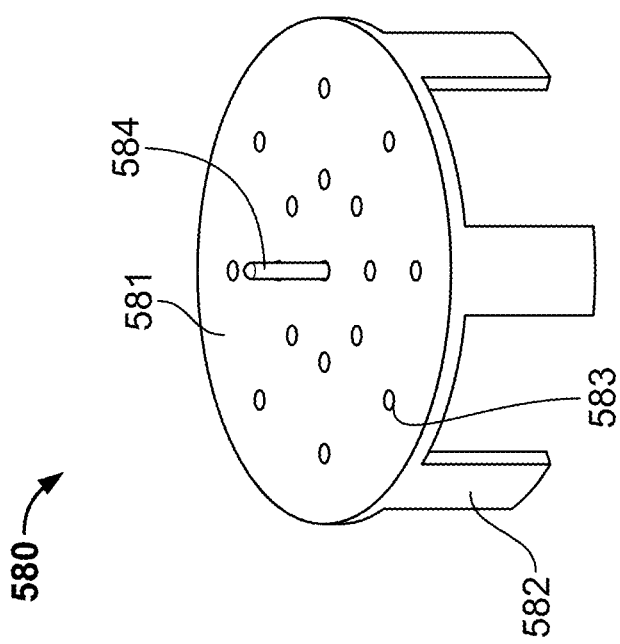
FIG. 5A shows a cover for a reservoir for holding a fragrant source, according to an embodiment of the present invention.

In FIGS. 5A and 5B covers 580, 585 are shown in relationship to a flameless candle 500, according to embodiments of the present invention. The covers 580, 585 may include top portions 581, 586, respectively. The covers 580, 585 may include legs 582, 587, respectively. The covers 580, 585 may include handles 584, 588, respectively. The handles 584, 588 may be located on the top portions 520, 525. In an embodiment, a handle may look like a wick, or a simulated wick (e.g. a portion designed to look like a conventional candle wick). A handle may allow a user to remove or place the cover 500 over a reservoir. A handle may allow a user to rotate the cover, including the legs.

In FIG. 5A, the cover 580 is depicted with perforations 583. In FIG. 5B, the cover 585 is illustrated to show the relationship of the top surface 586 and the legs 587. The top of the legs 587 extend outwardly (e.g., radially) from the top surface 586. When the cover 585 is inserted to cover the reservoir, a gap occurs between the top surface 586 and the sidewall of the housing.

FIGS. 5C and 5D show illustrative views of a flameless candle 500 including different covers 580, 585 for a reservoir for holding a fragrant source, according to an embodiment of the present invention. In FIG. 5C, the cover 580 (also depicted in FIG. 5A) is shown in relation to a housing 510 (similar to housings 210, 310, and 410). The vent holes 518 (similar to vent holes 218 and 318) allow an airflow from a hollow region (not shown) within the housing. The airflow then passes over the fragrant source (not shown) and through the perforations 582 in the cover 580. The airflow, having been infused with fragrance from the fragrant source, then passes into the living space atmosphere.

In FIG. 5D, the cover 585 (also depicted in FIG. 5B) is shown in relation to the housing 510. The vent holes 518 allow the airflow from a hollow region within the housing. As discussed in FIG. 5B, the top of the legs 587 extend outwardly from the top surface 586 of the cover 585. When the cover 585 is inserted to cover the reservoir, a gap between the top surface 586 and the sidewall of the housing 510 is formed, because the radius of the cover 585 is less than the radius of the reservoir. The airflow, having been infused with fragrance from the fragrant source, then passes into the living space atmosphere. Of course, the gap could be widened if the cover 585 had a smaller radius than the radius of the recessed area of the housing 510. Also, cover 580, depicted in FIGS. 5A and 5C could have a similar gap.

The legs of a cover serve to support and locate the top surface above the fragrant source. The legs also may control the amount of airflow. As represented in FIGS. 5C and 5D, the legs may be rotated to cover, block, or otherwise interfere with the airflow coming through the vent holes by varying degrees. For example, a user may use the handle of the cover to rotate the cover to increase or decrease the airflow. By controlling the amount of the airflow, it may be possible to control the intensity of the emitted fragrance from the candle.

Figure 6B:
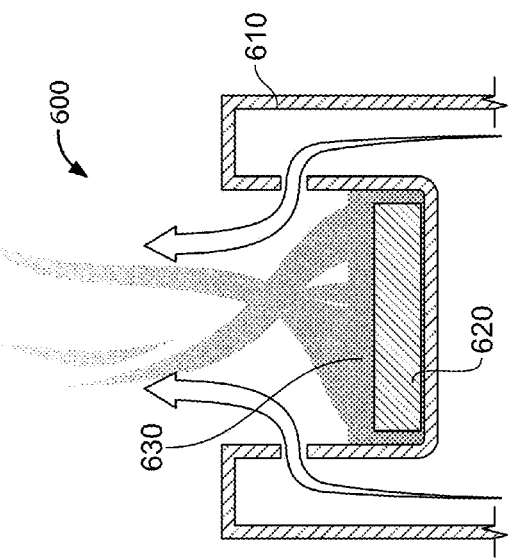
FIGS. 6A-6C illustrate an example of diffusion of a fragrant substance, according to an embodiment of the present invention.
Figure 6C:
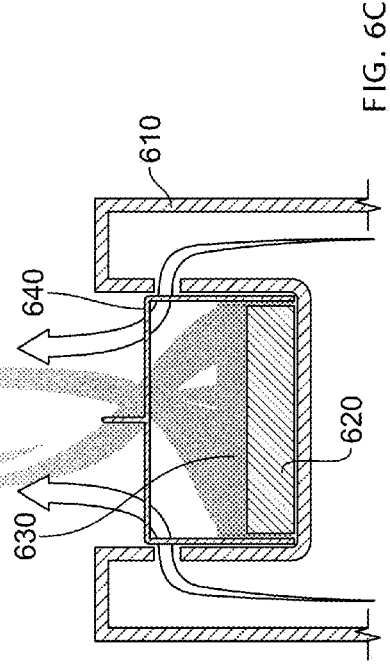
Figure 6A:
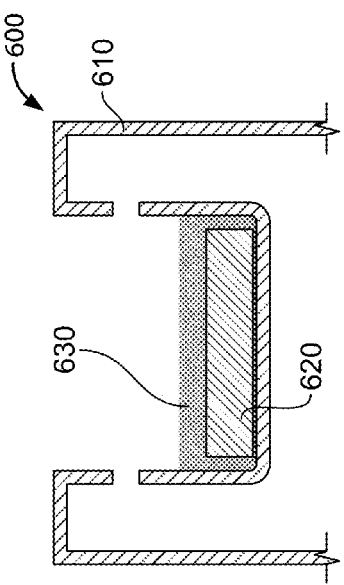

FIGS. 6A-6C illustrates an example of diffusion of a fragrant substance, according to an embodiment of the present invention. Generally speaking, fragrant substances may be rendered effective by exploiting or increasing the volatility (e.g., the vapor pressure) of the active portions and facilitating either passive diffusion (e.g., evaporation) into a living space atmosphere or forced distribution. Evaporation vapor pressure may be an important physical and chemical property intrinsic to a volatile fragrant chemical for populating either the immediate atmosphere (e.g., headspace) or the broader atmosphere of a particular targeted living space. Volatilization may take place spontaneously until the atmosphere is too crowded with the volatile ingredient or until the source is depleted. Positive evaporation vapor pressure follows thermodynamic laws exploiting physiochemical properties. The behavior of fragrant substances may depend on concentration gradients, surface tension, surface area, and/or temperature, for example. The chemical principle called the "LeChatelier principle" may influence how, in a given system, the fragrant substance may exhibit volatilization via diffusion pressure. Such volatilization may be influenced by the amount or type of material present in the source and the saturation level of the headspace.

Population of the headspace may increase through diffusion driven evaporation until a saturation point is reached or equilibrium is reached as defined by the conditions of temperature and among other conditions, the substrate, or molecular interactions of a given composition. Moving air over the source or perturbing the headspace through the Venturi effect depletes the population of fragrance chemicals in the headspace, and the natural laws drive more volatilization to replenish what was lost in the headspace.

FIG. 6A illustrates a flameless candle 600 before it is operated to diffuse a fragrant substance into the living space atmosphere. A housing 610 may have a recessed area that retains a fragrant source 620. The fragrant source may have a fragrant substance. Also, the recessed area may retain air in a headspace 630 above the fragrant source. The air in the headspace 630 may be at least partially saturated with the fragrant substance. When there is no airflow, the air in the headspace 630 may achieve equilibrium. At this stage, the air in the headspace 630 may be saturated with the fragrant substance. Because the air in the headspace 630 containing the fragrant substance is heavier than unfragranced air, it may sink or stay in a lower region of the recessed area. Under these conditions, the fragrant source or substance may be substantially sealed to the living space atmosphere because of the saturated air in the headspace 630.

FIG. 6B illustrates a flameless candle 600 while it is operated to diffuse a fragrant substance into the living space atmosphere. The recessed area may have a sidewall with a vent hole. The vent hole may hydrodynamically couple a hollow region within the housing and the recessed area. The vent hole is configured to allow an airflow from the hollow region and into the recessed area above the headspace. The airflow may be directed above the air in the headspace 630. For example, the airflow may not substantially flow into the air in the headspace 630 (or into or onto the fragrant source 620). The fragrant substance may be drawn from the air in the headspace 630 and into the airflow through the Venturi effect. The amount of fragrant substance drawn into the airflow may be regulated by increasing or decreasing the airflow. As the fragrant substance is removed from the air in the headspace 630, it may be replenished through diffusion from the fragrant source 620.

FIG. 6C is similar to FIG. 6B, except a cover 640 is also illustrated. The cover 640 may be similar to covers 480, 580, or 585. For example, the cover 640 may allow the airflow to pass into the living space atmosphere. The cover 640 may also be rotated to control the amount of airflow, as discussed in context of FIGS. 5C and 5D.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A flameless candle comprising:
   a housing including:
      a hollow region within the housing,
      a recessed area within a top surface of the housing, wherein the recessed area is bounded by a bottom surface and a sidewall, and
      a vent hole in the sidewall of the recessed area;
   a reservoir within the recessed area and configured to retain a fragrant source; and
   a lamp configured to emit a light upwardly through the bottom surface of the recessed area and upwardly through the fragrant source,
   wherein the vent hole is configured to allow an airflow from the hollow region and into the recessed area above the fragrant source.

2. The flameless candle of claim 1, wherein the housing comprises an eave configured to conceal the vent holes from being visible when the flameless candle is viewed from the top.

3. The flameless candle of claim 1, further comprising an outer shell encompassing the housing.

4. The flameless candle of claim 3, wherein the outer shell comprises an eave configured to conceal the vent holes from being visible when the flameless candle is viewed from the top.

5. The flameless candle of claim 3, wherein the outer shell comprises wax.

6. The flameless candle of claim 1, wherein the reservoir is integrated with the housing.

7. The flameless candle of claim 1, further comprising a cover configured to cover the reservoir, wherein a top surface of the cover defines a bottom surface of a well in the flameless candle.

8. The flameless candle of claim 7, wherein the cover comprises a handle on the top surface of the cover.

9. The flameless candle of claim 8, wherein the handle comprises a simulated wick.

10. The flameless candle of claim 7, wherein the cover comprises perforations configured to allow the airflow from the reservoir and into a living space atmosphere.

11. The flameless candle of claim 7, wherein:
    a radius of the top surface of the cover is less than a radius of the reservoir;
    a gap is formed; and
    the gap is configured to allow the airflow from the reservoir and into a living space atmosphere.

12. The flameless candle of claim 8, wherein the cover comprises a leg configured to:
    support the cover, and
    control the airflow through the vent hole in response to a rotation of the cover.

13. The flameless candle of claim 1, wherein fragrant source comprises a fragrant liquid.

14. The flameless candle of claim 13, further comprising a pad configured to provide the fragrant liquid to the airflow.

15. The flameless candle of claim 14, further comprising a wick to draw the fragrant liquid into the pad.

16. The flameless candle of claim 1, wherein the bottom surface of the reservoir comprises a raised portion configured to accommodate the lamp underneath the reservoir.

17. The flameless candle of claim 1, further comprising a base configured to engage with a bottom portion of the housing, wherein the base includes:
    feet configured to elevate the housing above a resting surface, and
    a hole configured to allow the airflow from a living space atmosphere and into the hollow region.

18. The flameless candle of claim 1, further comprising a fan configured to promote the airflow.

19. The flameless candle of claim 17, wherein the fan is positioned proximate to the base.

20. The flameless candle of claim 1, wherein:
    the housing further comprises a plurality of vent holes in the sidewall of the recessed area, and
    the plurality of vent holes is configured to allow the airflow from the hollow region and into the recessed area above the fragrant source.

21. The flameless candle of claim 20, wherein the plurality of vent holes encircle the sidewall of the recessed area.

22. A flameless candle comprising:
    a housing including:
    a hollow region within the housing,
    a recessed area within a top surface of the housing and comprising a sidewall, wherein the recessed area is configured to retain:
       a fragrant source including a fragrant substance, and
       a headspace above the fragrant source including air at least partially saturated with the fragrant substance, and
       a vent hole in the sidewall of the recessed area at least partially above a location for the fragrant source,
    wherein the vent hole is configured to allow an airflow from the hollow region and into the recessed area above the headspace.

23. The flameless candle of claim 22, wherein the airflow draws the fragrant substance from the air in the headspace through the Venturi effect.

* * * * *